United States Patent [19]

Fountain et al.

[11] Patent Number: 5,391,165
[45] Date of Patent: Feb. 21, 1995

[54] SYSTEM FOR SCANNING A SURGICAL LASER BEAM

[75] Inventors: William D. Fountain, Fremont; Carl F. Knopp, San Mateo, both of Calif.

[73] Assignee: Phoenix Laser Systems, Inc., Fremont, Calif.

[21] Appl. No.: 833,604

[22] Filed: Feb. 11, 1992

Related U.S. Application Data

[63] Continuation of Ser. No. 571,244, Aug. 22, 1990, abandoned.

[51] Int. Cl.⁶ .............................................. A61N 5/02
[52] U.S. Cl. ....................................... 606/4; 606/5; 606/10; 606/13; 359/196; 359/211
[58] Field of Search ............... 128/395, 397, 398; 606/2-19; 359/196, 211, 837

[56] References Cited

U.S. PATENT DOCUMENTS

| | | | |
|---|---|---|---|
| 2,975,668 | 3/1961 | Eckel | 359/211 |
| 3,226,721 | 12/1965 | Gould | 359/211 |
| 4,398,787 | 8/1983 | Balasubramanian | 350/6.4 |
| 4,414,684 | 11/1983 | Blonder | 350/6.4 |
| 4,718,418 | 1/1988 | L'Esperance, Jr. | 606/5 |
| 4,822,974 | 4/1989 | Leighton | 359/211 |

FOREIGN PATENT DOCUMENTS

| | | | |
|---|---|---|---|
| 1165448 | 10/1958 | France | 359/211 |
| 2333774 | 1/1974 | Germany | 350/6.4 |

*Primary Examiner*—David M. Shay
*Attorney, Agent, or Firm*—Thomas M. Freiburger

[57] ABSTRACT

In a laser beam delivery system for a surgical laser beam, steering and scanning of the laser beam along the target in transverse (X and Y) directions is accomplished in a mechanically simple and fast-responding manner. Closely adjacent to the objective lens assembly of the delivery system is a pair of prisms, i.e. a Risley prism or Herschel prism, positioned on the axis of the approaching laser beam. The two prisms, closely spaced, are mounted on separate rotating stages whereby they may be individually rotated about the beam axis. When the prisms are co-rotated, circular scans are produced on the target, in diameters depending on the angular phase between the prisms. Counter rotation of the prisms at equal and opposite speeds will produce a diametric line scan on the target. Any desired complex scan pattern can be achieved using combinations of rotations of the two prisms. Axial compactness and proximity to the objective lens assembly assure that virtually all of the angularly emerging beam from the prism pair passes through the objective lens assembly.

7 Claims, 3 Drawing Sheets

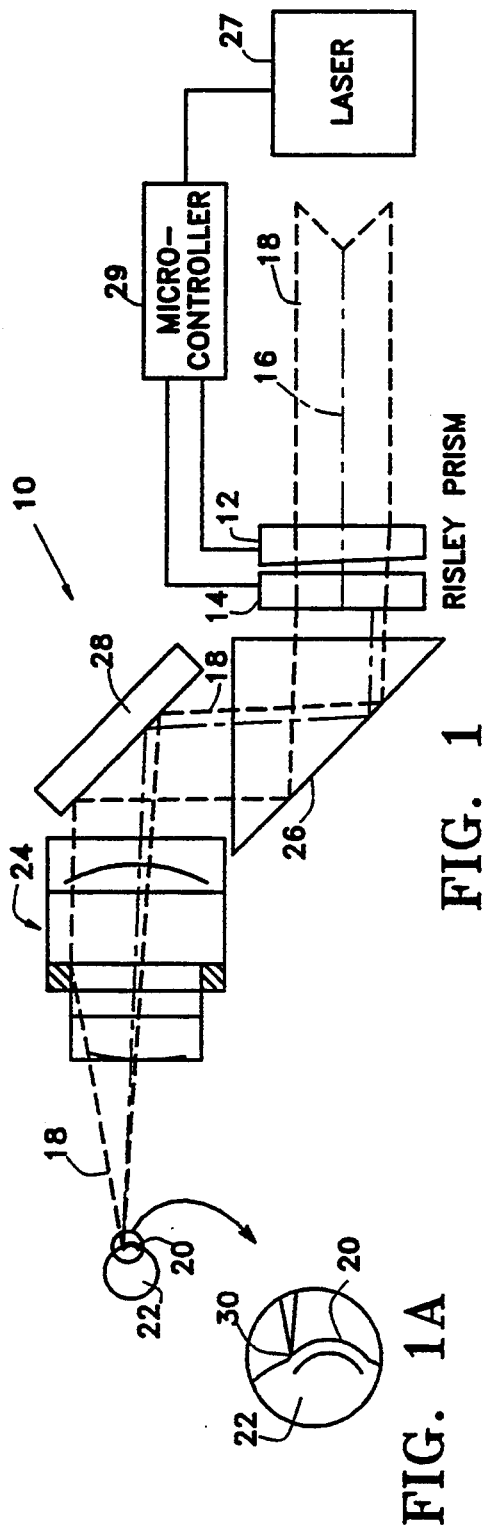
FIG. 1
FIG. 1A
SHORTER LEVER ARM GIVES BIGGER TREATMENT AREA
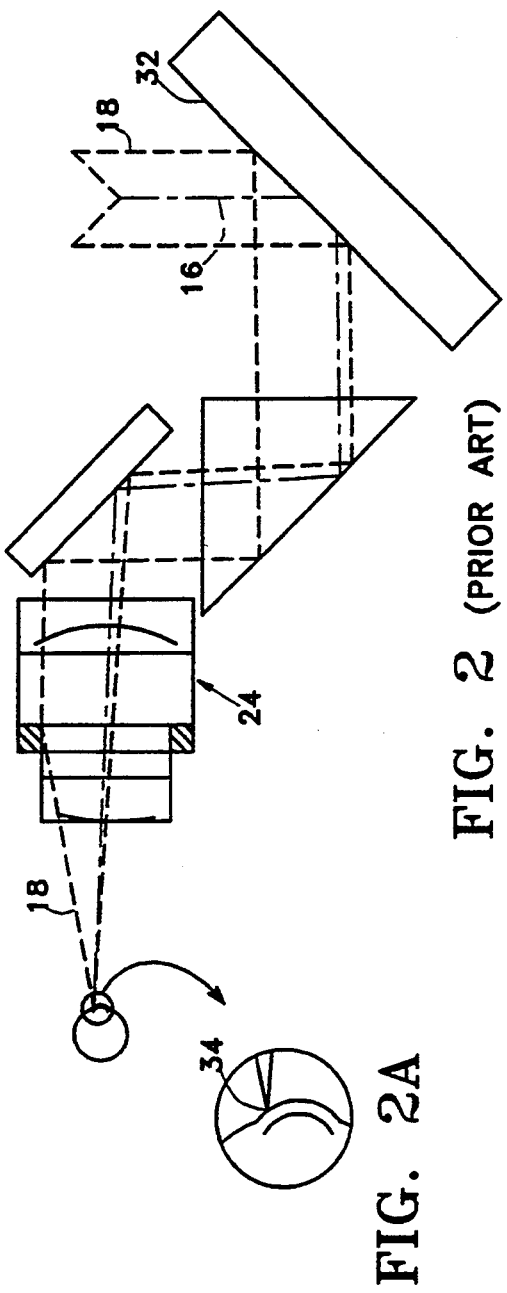
FIG. 2 (PRIOR ART)
FIG. 2A

CO-ROTATION:

BEAM CENTERLINE SWEEPS OUT A CONE (TRACES A CIRCLE)

COUNTER-ROTATION:

BEAM CENTERLINE SWEEPS OUT A PLANE (TRACES A LINE)

THE "NATURAL" PATTERNS OF THIS AIMING TECHNIQUE ARE THOSE DESIRED FOR TREATMENT

RADIAL KERATOTOMY

ARCUATE

TREPHINING

INTRASTROMAL PHOTODISRUPTION

SYSTEM FOR SCANNING A SURGICAL LASER BEAM

This is a continuation of co-pending application Ser. No. 571,244, filed on Aug. 22, 1990, abandoned.

BACKGROUND OF THE INVENTION

The invention relates to laser surgery apparatus, and in particular the invention is concerned with an improved laser beam delivery system for a surgical laser, wherein scanning and positioning the beam to points having transverse (X, Y) coordinates on the surgical target is accomplished more accurately and more efficiently.

Typically a surgical laser beam delivery system, to be manipulated in transverse directions along target tissue, i.e. in "X" and "Y" directions, must have some form of mechanical scanning component or components, usually behind an objective lens assembly. In most cases this function has been addressed by an internal mirror which is tiltable along two orthogonal rotational axes, under the control of servo motors. See, for example, copending U.S. patent application Ser. No. 475,657, filed Feb. 6, 1990 and assigned to the same assignee as the present invention.

Tilting mirrors can introduce inaccuracy into a surgical laser beam delivery system. A tilting mirror is secured at several mounting points and in addition is under the control of two different servo motors or galvo motors with linkages connecting to the mirror. With such a number of linkage components and points of mounting to base structure, there is a great potential for unwanted free movement or parts wear, and resulting inaccuracy in the tilt direction of the mirror. However, precision can be extremely important, particularly in eye surgery.

Another problem with the typical tilting mirrors is that they are normally positioned as close as practical to—but necessarily still a considerable distance from—the objective lens assembly of the system. This gives a longer lever arm for the tilted axis of the laser beam during scanning, resulting in either loss of some of the beam volume at the objective lens, or the need for a larger objective lens assembly to accommodate the swinging movements of the beam during scanning or positioning.

Further, the response time of a tilting mirror beam steering system, because of the relatively high moment of inertia thereof, can be somewhat slow and not always accurate for high speed ophthalmic surgery systems.

It is an object of the present invention described below to overcome these disadvantages and to provide an improved, more efficient and more accurate laser beam steering system.

SUMMARY OF THE INVENTION

In accordance with the present invention, a far simpler approach is presented for the problem of steering a surgical laser beam in transverse or X and Y directions, i.e. to points having transverse Cartesian coordinates (X, Y), or alternatively having cylindrical coordinates (r, theta). The steering method and components of this invention are simpler mechanically than the typical dual-motor apparatus which has been used to tip the plane of a mirror on two rotational axes simultaneously.

In the apparatus and method of the invention, steering and scanning of a surgical laser beam along a target in X and Y directions is accomplished in a simple and fast-responding manner. Closely adjacent to the objective lens assembly of the delivery system is a pair of optical wedges, i.e. wedged flats or prisms positioned on the axis of the approaching laser beam. The two wedges/prisms, closely spaced, are mounted on separate rotating stages whereby they may be individually rotated about the beam axis. Such a subassembly inherently has a much lower moment of inertia than the aforementioned tilting-mirror subassembly.

When the wedges/prisms are co-rotated with their thin ends together and their thick ends together, a circular scan is produced on the target, a useful scan in some forms of ophthalmic laser surgery. Circular scans of successively smaller radius may be achieved by adjusting the angular relationship of the two wedges/prisms, and again co-rotating the prisms.

Counter rotation of the prisms at equal and opposite speeds will produce a radial or diametric straight line scan on the target, another useful scan in some forms of ophthalmic laser surgery. The diametric line will be at an inclination which depends on the phase angle between the vertices of the prisms. Any desired complex scan pattern can be achieved using combinations of rotations of the two prisms.

The use of two wedged flats or prisms of this type, known as a Risley prism or a Herschel prism, has been a known technique in the laboratory. However, the laboratory use of the prisms was limited to setting a given aiming position of a laser beam, rather than dynamic scanning of the beam on a target.

Axial compactness and proximity to the objective lens assembly assure that all or virtually all of the angularly emerging beam from the prism pair passes through the objective lens assembly, and also that a greater field can be attained than is possible with a mirror used with the same objective.

Fast-responding motor devices of direct current, stepper or selsyn type individually operate the rotating stages of the two weak prisms, under the control of a microprocessor which selects the appropriate initial position and angular relationship of the two prisms. The motor devices then rotate the prisms in a sequence which will result in the path of the beam generating a two dimensional figure, from a single point to any degree of complexity desired, acting on the instructions of the microprocessor and the positional information returned by the motors.

In ophthalmic surgery, the prism assembly can fill a given area of a cornea with overlapping and concentric circles of lesions much faster than can a beam steering mirror, and many other surgical procedures can be effected quickly and efficiently.

It will be apparent that the descried apparatus and methods will also be useful in some industrial micromachinery applications. The discussion herein in terms of surgical applications is intended to be illustrative rather than limiting.

It is therefore among the objects of the invention to improve the efficiency, response time and mechanical simplicity of a steering procedure and apparatus in a surgical laser beam delivery system. These and other objects, advantages and features of the invention will be apparent from the following description of a preferred embodiment, considered along with the accompanying drawings.

DESCRIPTION OF THE DRAWINGS

FIG. 1 is a schematic view, which can be considered as a plan or elevation view, showing a portion of a surgical laser beam delivery system including a prism assembly for scanning the beam in accordance with the principles of the present invention.

FIG. 1A is a close up view showing the laser beam as delivered to the cornea using the present invention.

FIG. 2 is a view similar to FIG. 1, but indicating a prior art mechanism and method for scanning a surgical laser beam, in a beam delivery system similar to that shown in FIG. 1.

FIG. 2A is a close up view showing the laser beam as delivered to the cornea using the prior art.

DESCRIPTION OF PREFERRED EMBODIMENTS

Figures 3, 3A:
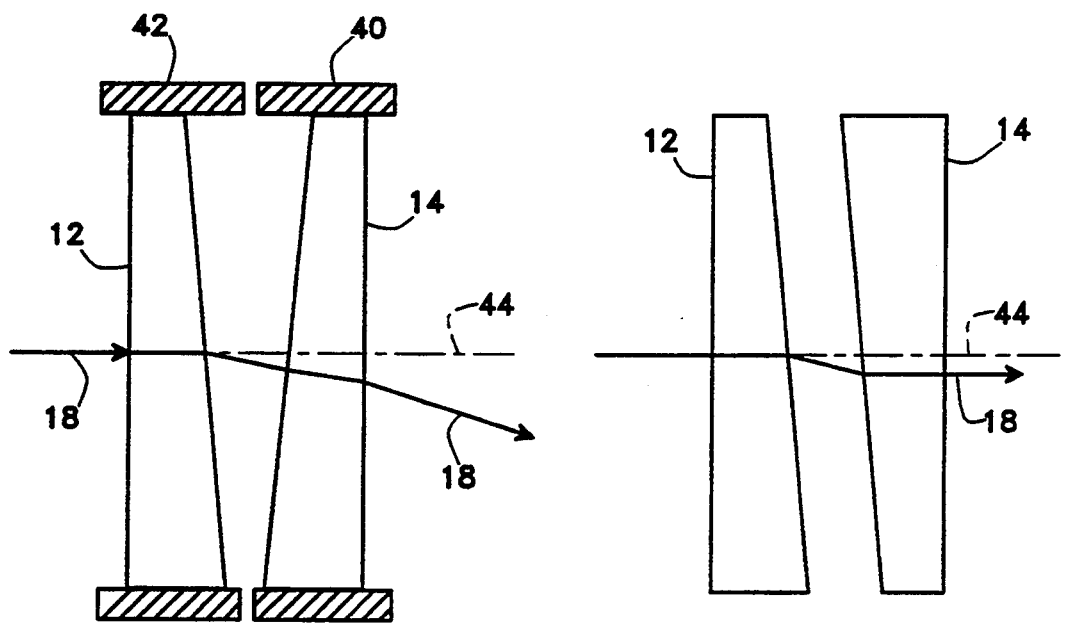
FIG. 3 is a schematic view showing a pair of rotatable wedges or prisms and indicating their axis of rotation, but with inclination of the wedge faces exaggerated.
FIG. 3A is a schematic view similar to FIG. 3, showing the two wedges in a different phase relationship.

In the drawings, FIG. 1 shows schematically a portion of a beam delivery system 10 including a pair of wedged flats or prisms 12 and 14. The weak prisms 12 and 14 are known collectively in the optical field as a Risley prism or a Herschel prism. The prisms are positioned concentrically on an optical axis 16 of a laser beam 18 which may be used for surgical operations on a target such as the cornea 20 of a patient's eye 22, as indicated in FIGS. 1 and 1A.

FIGS. 1, 1A, 2 and 2A demonstrate one advantage of the beam steering system of the present invention. The Risley prism, i.e. the prisms 12 and 14, are positioned very close to the objective lens assembly 24 of the beam delivery system 10. In the arrangement shown in FIG. 1, the Risley prism is shown directly and very closely behind a reflector or mirror 26 which may be—or be part of—a beam splitter for passing light from the objective onto another optical axis in the system. Thus, another mirror or reflector 28 is directly adjacent to the objective 24. It is conceivable that in some systems, the Risley prism 12, 14 could be directly adjacent to the objective 24 itself.

FIG. 1 shows that the beam 18 is not clipped by the objective 24 in its path toward the cornea 20. The figure shows the beam focussed at a point 30 which is at an extreme position in the transverse range of the beam (a maximum upward position as shown in the drawing). In FIG. 2, showing a two-axis tiltable beam steering mirror 32 such as typically used in conventional beam delivery systems, the laser beam 18 is likewise shown focussed and directed at a maximum upward position, i.e. the maximum position which will avoid clipping and loss of beam volume through the objective assembly 24. However, in this arrangement the maximum position 34 of the beam is less extreme than in FIG. 1, resulting in a smaller lateral field within which the beam 18 can operate. This is due to the increased distance behind the objective 24 which is necessary for the tilting mirror 32, as opposed to the Risley prism 12, 14 in FIG. 1. A longer lever arm from the tilting mirror to the objective causes a situation wherein a smaller angle of the beam will result in clipping.

FIG. 1 also indicates a laser source 27 and a microprocessor or microcontroller 29. The controller 29 is schematically indicated as controlling the rotation of the Risley prism, i.e. the pair of prisms 12, 14, and also controlling the firing of the laser source 27 to produce the beam. As explained further below, the timing of laser firing is coordinated with the rotations of the prisms 12 and 14 to produce desired patterns traced at the target by the laser beam 18.

FIGS. 3 and 3A show the effects of angular orientation and rotation of the prisms or wedged flats 12, 14 of the Risley prism pair. In both FIGS. 3 and 3A the angle between the front and back faces of each prism is shown exaggerated. In actual practice, each prism can have an angle of about 1° between its front and back faces, for serving the purposes of one embodiment of an ophthalmic surgical beam delivery system. The prisms are schematically shown as mounted on rotating stages or motors 40 and 42, for rotation about a rotational axis 44.

In FIG. 3 the prisms 12 and 14, each of which is independently rotatable, are shown in an angular relationship wherein the thinner ends are together and the thicker ends are together. This is a position producing a maximum angulation of the laser beam 18, originally parallel to the rotational axis, as it passes through both prisms. If the two prisms 12, 14 are rotated together in this position, or co-rotated, it can be seen that a circle will be traced with the laser beam on the target. The maximum angular orientation, which is shown in FIG. 3, will generate the largest diameter circle with the beam.

FIG. 3A shows the prisms 12.14 in an angular relationship which is 180° opposite what is shown in FIG. 3, i.e. the prisms are positioned with thin end opposite thick end. Since the prisms 12 and 14 have the same prism angle, the laser beam 18, entering parallel, also emerges parallel. A slight translational offset is produced, as indicated, but since the beam 18 is parallel going into the objective, this will have no effect on the system. Parallel light will still be focussed to the focal point 30 (FIG. 1). Nonetheless, the prisms are positioned as close together as possible in order to obviate clipping at the objective.

Thus, it can be seen that if the prisms 12 and 14 are co-rotated (rotated maintaining the same angular relationship or phase) about the rotational axis 44, with a phase which is between the maximum positions shown in FIGS. 3 and 3A, a smaller circle will be generated at the target with the laser beam. The relative phase between the two prisms in such co-rotation will determine the diameter of the circle traced at the target, or the angular diameter of beam sweep which is swept by the beam.

Figure 4:
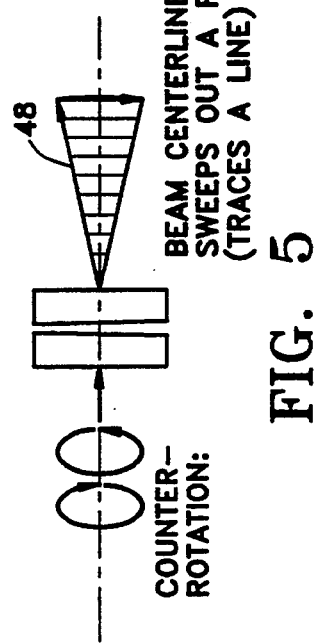
FIG. 4 is a schematic elevation view indicating the rotatable wedges and the effect of co-rotation of the wedges.

FIG. 4 schematically demonstrates co-rotation, and the resulting cone 46 which is swept by the beam. It is the angle of this cone 46 which is adjusted by adjustment of the phase angle between the prisms 12, 14.

Figure 5:
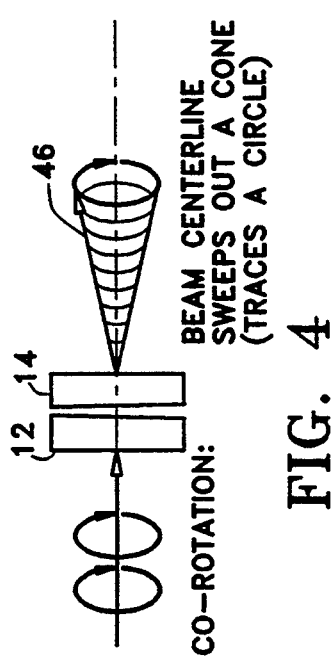
FIG. 5 is a schematic view similar to FIG. 4, but showing the effect of counter-rotation of the wedges.

If the prisms 12 and 14 are counter rotated about the rotational axis 44, at equal rotational speeds, a diametric line will be traced at the target. FIG. 5 schematically indicates counter rotation, with the beam center line sweeping a plane 48, therefore tracing a line on the target.

This effect can be seen from FIGS. 3 and 3A. If FIG. 3A is considered a starting position (0°), and each prism is then rotated through 90° in opposite directions, this will result in a 180° phase relationship as represented in FIG. 3, but the angular position of the two prisms will be 90° from what is seen in FIG. 3. Therefore the sweep of the plane, and the trace of the line on the target, will be in and out of the paper as regards FIG. 3.

Rotation of one prism while the other is kept stationary will trace a circle, but one which is off-axis. Shifting of the angular position of the other prism will change the location of the off-axis circle.

Thus, it can be seen that with combinations of co-rotation and counter rotation, any type of pattern can be traced on the target. If line traces are desired, the azimuth of the line can be selected by co-rotation to the proper point, then counter rotation. Shorter or longer lines can be traced simply by energizing the laser at the proper times and for the proper periods during prism rotation. The desired patterns can be accomplished using programming in a microprocessor, which can readily be carried out by those skilled in the art and which does not form a specific part of the present invention.

FIGS. 6 through 10A illustrate various laser traces which are desirable for certain types of ophthalmic surgery. In all of these illustrations the ophthalmic surgery is directed to the cornea 20.

Figure 6:
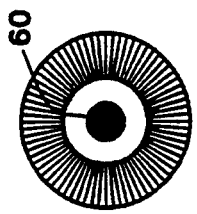
FIG. 6 is a schematic frontal view showing a cornea and surrounding iris of an eye, and indicating a surgical lesion pattern on the cornea for a radial keratotomy procedure, which can be achieved with the beam steering apparatus of the invention.
Figure 6A:
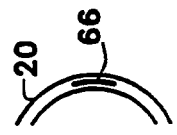
FIG. 6A is a partial schematic sectional view in elevation, indicating some of the corneal lesions shown in FIG. 6.

Radial lines, which are achievable by counter rotation as discussed above, are the type of laser cuts needed for radial keratotomy, as illustrated in FIGS. 6 and 6A. FIG. 6 shows radial, i.e. partial diametric cuts 50 made at three different angles around the cornea. As mentioned above, these three different angles are set by co-rotating the prisms to the proper point, before energizing the laser, then counter rotating. Further, in order to begin a cut or trace at the desired point, the two prisms will have to be at the proper phase relationship with each other before counter rotation is begun. If a cut 50 such as shown in FIG. 6 is to be started at the outer edge of the cornea, for example, and such point is the maximum of the beam's range for the particular patient positioning, etc., then the phase angle of the two prisms should be as shown in FIG. 3 to start at a maximum beam sweep point. The prisms can first be moved by counter rotation to this phase relationship, then co-rotated to set the proper cut line azimuth. Then, with the laser energized, the prisms can be counter rotated at equal speeds. Each full counter rotation of both prisms will produce a back and forth diametric sweep. To produce the radial cuts 50 as shown in FIG. 6, the laser beam is shut off when the sweep is over the center portion 52 of the cornea.

Figure 7:
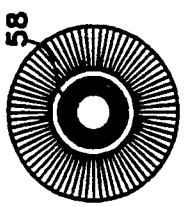
FIG. 7 is a view similar to FIG. 6, but showing a pattern of lesions for an arcuate keratotomy procedure.
Figure 8:
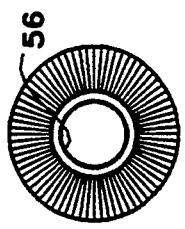
FIG. 8 is another view similar to FIG. 6, but showing a circular pattern of surgical lesions on the cornea, for a trephining procedure in ophthalmic surgery.
Figure 7A:
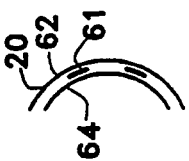
FIG. 7A is a view similar to FIG. 6A, but showing the lesion pattern indicated in FIG. 7.
Figure 8A:
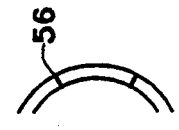
FIG. 8A is a sectional view similar to FIG. 6A, showing the lesion pattern of FIG. 8.

FIGS. 7 and 7A show arcuate corneal cuts 54 for arcuate keratotomy. FIG. 8 shows a circular trephining cut 56.

Figures 9, 10:
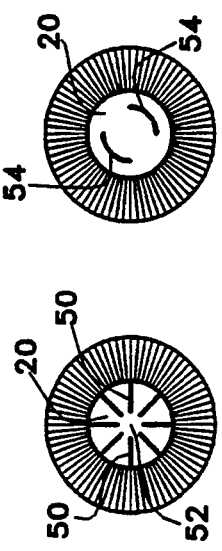
FIG. 9 is another view similar to FIG. 6, showing a filled-circle pattern of lesions defining an annulus of concentric circles on the cornea, in an intrastromal photodisruption technique (for far-sightedness correction).
FIG. 10 is a view similar to FIG. 9, but showing a filled-circle pattern of circular concentric lesions in a smaller series of diameters, again in intrastromal photodisruption (but for near-sightedness correction).
Figure 9A:
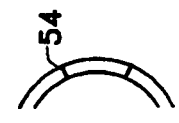
FIG. 9A is a sectional view indicating the lesion pattern shown in FIG. 9.

FIGS. 9 and 10 indicate the machining of annuluses or discs of intrastromal photodisruption in the cornea, another procedure for changing the shape of the cornea. To generate the groups of circles 58 or 60 associated with this procedure, the prisms 12, 14 are co-rotated through one revolution, then their phase is changed by one step, and they are then co-rotated through another revolution to produce the next circular cut. If this procedure is repeated for a succession of smaller circles as indicated in FIG. 9, an annulus 61 of photodisruption will be generated inside the cornea, between the epithelial and endothelial layers 62 and 64, as shown in FIG. 9A.

Figure 10A:
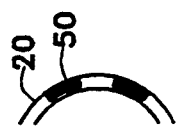
FIG. 10A is a schematic sectional view showing the lesion pattern of FIG. 10.

If the succession of circles is repeated to zero diameter, a disc 66 of photodisruption will be produced inside the cornea 20, as shown in FIG. 10A.

The concentric circles 58 or 60 in these procedures should be overlapping so that a solid mass of cornea tissue is disrupted. This creates a pocket or void inside the cornea, of a selected shape. The gas inside this void area is rapidly resorbed by the body and the void collapses, thereby changing the local surface contour of the cornea over that location.

It can be seen that by proper combinations of co-rotation and counter rotation of the two wedged flats or prisms 12 and 14, any point can be reached within the largest diameter circle which can be drawn with the beam. If the radius of a given position is referred to as r and the angle to that position as theta, any combination of r, theta can be reached within the largest possible circle, and this is of course equivalent to reaching any point in a set of Cartesian coordinates X, Y within that same circle.

Figure 11:
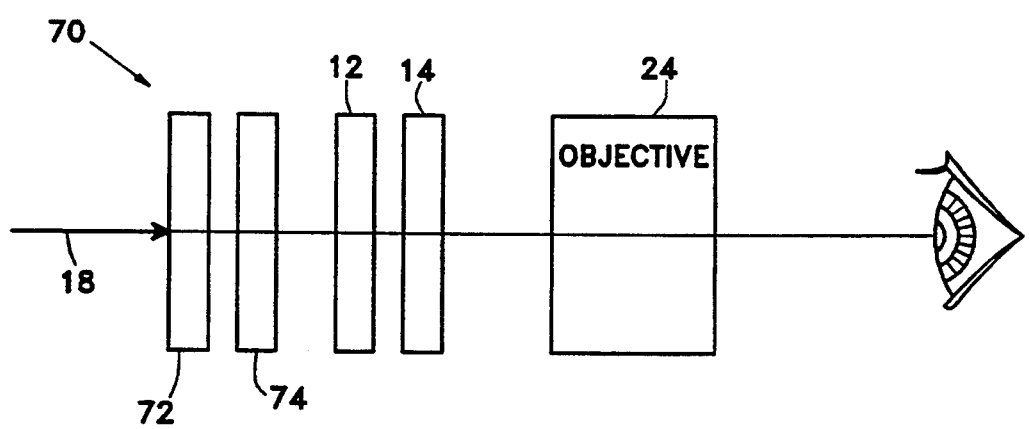
FIG. 11 is a schematic view showing a variation of the system and method of the invention, wherein two prism pairs are included.

FIG. 11 is another schematic view which illustrates an addition or variation to what is shown and described above. A second Risley prism pair 70 comprising prisms 72 and 74 may be serially positioned along the laser beam axis 18, upstream or downstream from the prism pair 12, 14. This enables useful patterns such as small circles to be efficiently and quickly traced off the center of the eye. In the arrangement shown in FIG. 11, the Risley prism pair 70 can be used for locating a desired pattern to a selected position on the eye—for example, the center of a small circle to be traced. The downstream Risley prism pair 12, 14 can be used to trace the actual pattern or patterns dynamically. This is particularly useful for the tracing of off-axis circles. Although, as emphasized above, the prism pair 12, 14 can be used to trace any pattern, from any point to any other point, the speed of such patterns is limited by the need for stopping, starting and reversing the direction of rotation of each of the prisms 12, 14.

However, when a circle or a series of circles is to be generated off-axis on the eye, the orderly spinning of the prisms 12, 14 can be maintained to generate the circles of lesions, while the back prism pair 70 can be used to locate the circles as desired. In this way, high speed operation can be effected for non-symmetrically located patterns on the eye.

The above described preferred embodiment is intended to illustrate the principles of the invention, but not to limit its scope. Other embodiments and variations to this preferred embodiment will be apparent to those skilled in the art and may be made without departing from the spirit and scope of the invention as defined in the following claims.

We claim:

1. In a laser delivery system including a laser producing a laser beam directed along a path, and optics including an objective lens for delivering the beam toward a target to be operated upon by the laser beam, a beam steering assembly for directing the laser beam through appropriate patterns traced on the target to effect a particular operation on the target as selected, comprising, a pair of adjacent weak prisms positioned serially in the path of the laser beam, rotating stage means including a rotating stage connected to each prism for enabling rotation of each of the prisms, either together or relative to one another, about a common axis generally aligned with the path of the laser beam approaching the prisms, and motor means connected to each rotating stage for individually controlling and varying the rotational position and the direction and speed of rotation of each prism independently, whereby the rotational position and the direction and speed of rotation of each prism may be independently controlled in accordance with a selected location and pattern desired for tracing of the laser beam on a target, including radial traces, non-radial linear traces, circular or elliptical traces and any other combination of translation and/or rotation of the beam across the target.

2. In an ophthalmic surgical laser delivery system including a laser producing a laser beam directed along a path, and optics including an objective lens for delivering the beam toward an ocular target in an eye and for producing a focus, a beam steering assembly for directing the laser beam through appropriate patterns in the eye as selected, to produce laser-induced changes to the ocular target in the eye, comprising, a pair of adjacent weak prisms positioned serially in the path of the laser beam, rotating stage means including a rotating stage connected to each prism for enabling independent rotation of each of the prisms, either together or relative to one another, about a common axis generally aligned with the path of the laser beam approaching the prisms, motor means connected to each rotating stage for individually controlling the rotation of the prisms, and beam steering control means connected to the motor means for controlling and varying the rotational position and the direction and speed of rotation of each prism independently and in relation to the other prism in accordance with a selected location and pattern desired for moving the focus of the laser beam on the ocular target in a surgical procedure, including radial traces, non-radial linear traces, circular and elliptical traces and any other combination of translation and/or rotation of the beam across the ocular target.

3. Apparatus according to claim 2, wherein the pair of prisms are closely adjacent to the objective lens, whereby angular variation of the path of the beam exiting the pair of prisms causes only minimal loss of beam volume entering the objective lens.

4. Apparatus according to claim 3, further including a second pair of prisms positioned serially in the path of the laser beam, with second rotating stage means connected to the prisms of the second pair for enabling individual rotation of each of the second pair of prisms, either together or relative to one another and the first pair of prisms, about an axis generally aligned with the path of the laser beam approaching the second pair of prisms, second motor means connected to each rotating stage of the second rotating stage means, for individually controlling the rotation of the prisms of the second pair, and said beam steering control means being connected to the second motor means for control of the rotations of the second pair of prisms, whereby the second pair of prisms may be used for relocating the center of a beam pattern generated by said pair of adjacent weak prisms.

5. A method for positioning and steering in transverse directions a focused laser beam directed along a path to a target, and for producing selected patterns traced on the target, comprising, positioning a pair of adjacent prisms serially in the path of the laser beam, the prisms being mounted on rotating stages with motor means connected to each rotating stage for individually controlling rotation of the prisms about a common axis generally aligned with the path of the laser beam, and controlling the motor means so as to control and vary the rotational position and the direction and speed of rotation of each prism independently and with respect to the other prism in accordance with a selected location and pattern desired for tracing the laser beam on a target, whereby the rotating prisms may be used to generate radial traces, non-radial linear traces, circular and elliptical traces and other combinations of translation and/or rotation of the laser beam across the target.

6. The method of claim 5, wherein the target is the cornea of the eye of a living being, with the beam being traced in a desired pattern of desired ophthalmic surgery on the cornea.

7. The method of claim 6, wherein the step of controlling the motor means includes controlling and varying the rotational position and the direction and speed of rotation of each prism independently in such a way as to steer the focus of the laser beam through all locations within a selected area on the target.

* * * * *